United States Patent [19]

Yeng et al.

[11] Patent Number: 5,840,991

[45] Date of Patent: Nov. 24, 1998

[54] ANTIATHEROSCLEROSIS AGENTS FOR LIPID-LOWERING AND ANTIPEROXIDATIVE ACTIVITY

[75] Inventors: Feng-Wen Yeng; Shan-Shue Wang; Jaw-Yuh Chiu; Chin-Fen Lee; Chia-Lin J. Wang, all of Taipei, Taiwan

[73] Assignee: Development Center for Biotechnology, Taipei, Taiwan

[21] Appl. No.: 932,030

[22] Filed: Sep. 17, 1997

Related U.S. Application Data

[63] Continuation of Ser. No. 787,090, Jan. 22, 1997, abandoned.

[51] Int. Cl.$^6$ .......................... C07L 315/00; A01N 41/10
[52] U.S. Cl. ................... 568/32; 568/52; 568/54; 514/706; 514/712; 514/708; 514/709
[58] Field of Search .................. 568/32, 52, 54; 514/706, 708, 709, 712

[56] References Cited

U.S. PATENT DOCUMENTS

| | | |
|---|---|---|
| 5,281,714 | 1/1994 | Fobare et al. . |
| 5,304,668 | 4/1994 | Parker et al. . |
| 5,330,998 | 7/1994 | Clark et al. . |
| 5,352,677 | 10/1994 | Fuse et al. . |
| 5,369,123 | 11/1994 | Santafianos et al. . |
| 5,411,969 | 5/1995 | Pearce et al. . |

FOREIGN PATENT DOCUMENTS

| | | |
|---|---|---|
| 154115 | 6/1974 | Czechoslovakia . |
| 332331 | 9/1989 | European Pat. Off. . |
| 571928 | 12/1993 | European Pat. Off. . |
| 1-295885 | 11/1989 | Japan . |
| WO 9420456 A1 | 9/1994 | WIPO . |

OTHER PUBLICATIONS

Xu, C et al, Chin. Chem. Lett (1993), 4(12) 1051–2.

*Primary Examiner*—Paul J. Killos
*Attorney, Agent, or Firm*—McDonnell Boehnen Hulbert & Berghoff

[57] ABSTRACT

The invention relates to novel compounds of formula (I)

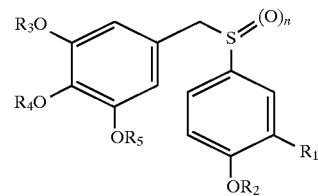

wherein
  $R_1$ represents hydrogen, hydroxy or alkoxy;
  $R_2$, $R_3$, $R_4$ and $R_5$ may be hydrogen or alkyl; and
  n is 0,1 or 2;
and the pharmaceutically acceptable salts thereof.

The invention also relates to the processes for preparing the compounds of formula (I), and the pharmaceutical compositions containing them, and their use as a low density lipoprotein peroxidation inhibitors, anti-atherosclerotic agents and/or antihyperlipidemic agents.

13 Claims, No Drawings

ANTIATHEROSCLEROSIS AGENTS FOR LIPID-LOWERING AND ANTIPEROXIDATIVE ACTIVITY

This application is a continuation, of application Ser. No. 08/797,090, filed Jan. 22, 1997, now abandoned.

FIELD OF THE INVENTION

The present invention relates to novel compounds useful as low Density Lipoprotein (LDL) peroxidation inhibitors, anti-atherosclerotic agents, anti-hyperlipidemic agents and/ or antihypercholesterolemic agents.

BACKGROUND OF THE INVENTION

Cardiovascular diseases remain the major cause of death in most industrialized countries of the world. Atherosclerosis is the principle cause of the pathogenesis of myocardial and cerebral infarction which accounts for the majority of deaths due to cardiovascular diseases. In the United States, it is estimated that 550 thousand people die of atherosclerosis-induced myocardial infarction each year. In 1991, statistics indicate that cardiovascular disease due to atherosclerosis is the number one cause of death in Japan. Epidemiological studies have shown that atherosclerosis results from many risk factors such as hypercholesterolemia, hyperlipidemia, hypertension, smoking, etc. It is believed that hypercholesterolemia is the most serious risk factor of atherosclerosis lesion. Serum cholesterol is classified into categories such as LDL and high-density lipoprotein (HDL). While the presence of LDL-cholesterol promotes the deposition of cholesterol onto arterial walls, HDL-cholesterol transports excess cholesterol from the peripheral blood vessels and returns to the liver, thereby preventing the deposition of cholesterol onto the arterial walls. Thus, susceptibility of the arterial wall to the accumulation of cholesterol is governed by the total serum cholesterol concentration, and by the ratio of LDL to HDL. Several reports have demonstrated that risk of myocardial infarction or atherosclerosis is decreased by reducing LDL cholesterol level and increasing HDL.

An understanding of the process of atherosclerosis pathogenesis at a molecular regulation level is beneficial for developing new antiatherosclerosis agents.

One generally well accepted theory of atherosclerosis formation is "the response to injury theory" of pathogenesis, which suggests a denudation of blood vessel endothelial cells may be related to the initiation of atherosclerosis pathogenesis. Thus blood vessel endothelium cell dysfunction can be caused by physical injury (notably at branched points in the arterial tree), by the risk factors listed above, by mechanical stress, or by certain chemical species in the blood. Once dysfunction has occurred, the platelets, monocyte or T-lymphocyte are recruited to the injury area and penetrate into the subendothelial intima. In the intima, the monocyte differentiates into macrophages and devours modified -LDL cholesterols to form foam cells. Some of the foam cells may move back into the blood stream, but most of the foam cells remain and eventually die leaving a massive amount of cholesterol in the intima resulting in arterial thickening. The smooth muscle cell also migrate into the intima, and proliferate to produce another form of arterial thickening. An endothelial cell dysfunction also causes a permeation of LDL cholesterol and related lipoprotein into the intima. During the atherogenesis process, the arterial thickness slowly increases by accumulation of lipids (mainly cholesterol), foam cell and smooth muscle cell to become a fatty streak and subsequently forms fibrous plaque. The fibrous plaque continues to increase in size and finally intrudes into the arterial lumen to interfere with the blood flow.

The oxidative modification of LDL may play an important role in atherosclerosis. The "oxidized LDL hypothesis" proposes that the native LDL is not recognized by scavenger receptors and does not cause the cholesterol accumulation, but in fact oxidized LDL is taken up via macrophage scavenger receptor and leads to pathogenic cholesterol accumulation. Oxidized LDL is also cytotoxic to the cells, which may be an important factor leading to damage of the endothelium cell. Recently, antioxidant agents have been demonstrated to prevent LDL oxidation and to reduce the rate of atherosclerosis progress in animal experiments and clinical patient studies. This new category of antiatherosclerosis agents has been described to prevent atherosclerosis by inhibiting the lipid oxidation, but not lipid-lowering mode.

For the treatment of hypercholesterolemia, several drugs against cholesterol risk factors have been developed and applied in clinical use. For example HMG-CoA reductase inhibitors such as simvastatin, pravastatin, and lovastatin have effectively reduced blood cholesterol level by blocking the cholesterol synthesis. Fibric acid derivatives include gemfibrozil and clofibrate decrease the blood cholesterol and triglyceride levels. Bile acid sequestrants such as cholestyramine and colestid reduce the blood cholesterol by inhibiting cholesterol reabsorption. Nicotic acid is also effective in lowering the total cholesterol and LDL cholesterol and increasing the HDL cholesterol. Probucol is believed to achieve the lowering of hypercholesterolemia by reducing the plasma cholesterol and by preventing the lipoprotein oxidation. (Koyo Matsuda, Medical Research Review, 1994).

All patents recited herein are hereby incorporated by reference in their entirety and in their specific pertinent parts.

U.S. Pat. No. 5,281,714 disclosed dioxoheterocyclohexanedione derivatives, which are said to be anti-oxidants that may be useful in treating atherosclerosis and hypercholesterolemia.

U.S. Pat. No. 5,304,668 disclosed certain bis-[4-(2,6-dialkyl)phenol]silane derivatives, which are anti-oxidants said to be useful as LDL inhibitors and in treating atherosclerosis.

U.S. Pat. No. 5,330,998 disclosed thiazolidine-2,4-dione derivatives, which lower cholesterol levels and may be useful for treatment of hypercholesterolemia.

U.S. Pat. No. 5,352,677 described cinnamamide derivatives useful in the treatment of hyperlipidemia and arteriosclerosis.

U.S. Pat. No. 5,369,123 disclosed naphthalene derivatives useful for inhibiting cholesterol biosynthesis in the treatment and prevention of hypercholesterolemia.

WO 9,420,456-Al disclosed stilbene derivatives and analogs thereof as 1,2-lipoxygenase inhibitors said to be useful for treating arteriosclerosis and circulatory disorders.

SUMMARY OF THE INVENTION

The compounds of the are novel antiatherosclerosis agents which are useful in lowering total serum cholesterol and LDL levels, effectively elevating HDL level, and useful for inhibiting and treating hyperlipidemia, hypercholesterolemia and atherosclerosis.

The present invention provides a novel compound of the general formula (I):

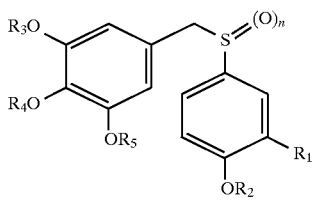

Formula (I)

wherein

R₁ represents hydrogen, hydroxy or alkoxy;

R₂, R₃, R₄ and R₅ may be hydrogen or alkyl; and n is 0,1 or 2;

and the pharmaceutically acceptable salts thereof.

Surprisingly. it was found that the compound of formula (I) is an effective inhibitor of LDL-peroxidation. Accordingly, in another aspect of the invention, there is provided pharmaceutical compositions for use as an LDL-peroxidation inhibitor, anti-atherosclerotic agent, anti-hyperlipidemic and/or anti-hypercholesterolemic agent comprising the compound of formula (I) as the active ingredient.

The present invention further provides methods for preparing the compound of formula (I), which comprises:

(1) thioalkylating, under an alkaline condition, a 3,4,5-trialkoxybenzyl halide of formula (II)

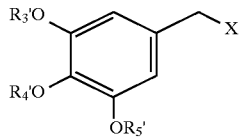

Formula (II)

wherein R₃',R₄' and R₅' are each alkyl and X is halogen, with a thiophenol derivative of formula (III)

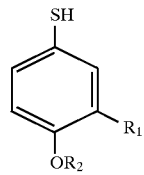

Formula (III)

wherein R₁ is hydrogen, hydroxy or alkoxy, and R₂ is hydrogen or alkyl, to produce the compound of formula (I) wherein R₃, R₄ and R₅ are each alkyl and n is 0;

(2) if necessary, oxidizing the compound of formula (I) wherein R₃, R₄ and R₅ are each alkyl and n is 0 with a suitable oxidizing agent to give a corresponding compound of formula (I) wherein n is 1 or 2;

(3) if necessary, dealkylating a compound of formula (I) wherein R₂, R₃, R₄ and R₅ are each alkyl to give a corresponding compound of formula (I) wherein R₂, R₃, R₄ and R₅ may be the same or different and at least one of them is hydrogen; and (4) if necessary, converting the compound of formula (I) into corresponding pharmaceutically acceptable salts thereof.

DETAILED DESCRIPTION OF THE INVENTION

As used herein, the term "alkyl" refers to a straight or branched alkyl group having 1 to 8 carbon atoms, which may be methyl, ethyl, propyl, isopropyl, butyl, isobutyl, 1-methylpropyl, tertiary butyl, pentyl, isopentyl, neopentyl or the like. As used herein, the term "alkoxy" refers to a straight or branched alkoxy group having 1 to 8 carbon atoms, which may be methoxy, ethoxy, propoxy, butoxy or the like.

As used herein, the term "halogen" includes fluorine, chlorine and bromine.

Examples of the compounds of formula (I) include, but are not limited to:

3,4,5-trimethoxybenzyl 4-hydroxyphenyl thioether;
3,4-dihydroxy-5-methoxybenzyl 4-hydroxyphenyl thioether;
3,4,5-trimethoxybenzyl 4-hydroxyphenyl sulfoxide;
3,4,5-trihydroxybenzyl 4-hydroxyphenyl thioether;
4-hydroxy-3,5-dimethoxybenzyl 4-hydroxyphenyl thioether;
3,4,5-trimethoxybenzyl 3,4-dimethoxyyphenyl thioether; and
3,4,5-trihydroxybenzyl 3,4-dihydroxyphenyl thioether.

The compound of formula (I) can be synthesized using techniques well known in the art.

For example, the compound of formula (I) wherein R₃, R₄ and R₅ are simultaneously alkyl and n is 0 can be produced by thioalkylating, under an alkaline condition, the 3,4,5-trialkoxybenzyl halide of formula (II)

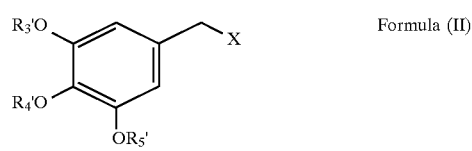

Formula (II)

wherein R₃', R₄' and R₅' are each alkyl and X is halogen, with the thiophenol derivative of formula (III)

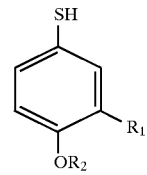

Formula (III)

wherein R₁ is hydrogen, hydroxy or alkoxy and R₂ is hydrogen or alkyl.

Bases suitable for use in the above reaction include, but are not limited to: carbonates and hydroxides of alkaline metals, such as potassium carbonate, sodium carbonate, sodium hydroxide, etc.

For increasing the selectivity of thioalkylation, the reaction is preferably carried out at a low temperature, e.g. at −10° to 20°C., and most preferably at 0° to 10° C.

The compound of formula (I) wherein n is 1 or 2 can be prepared by oxidizing a corresponding compound of formula (I) wherein R₃, R₄ and R₅ are each alkyl and n is 0 with a suitable oxidant.

Oxidants suitable for use in the reaction include, but are not limited to: hydrogen peroxide, potassium permanganate, potassium perchromate and 3-chloroperoxybenzoic acid (MCPBA), etc.

The compound of formula (I) wherein at least one of R₂, R₃, R₄ and R₅ is hydrogen can be prepared by appropriately dealkylate a corresponding compound of formula (I) wherein R₂, R₃, R₄ and R₅ are each alkyl.

Dealkylating agents suitable for use in the reaction include, but are not limited to: trihaloboron, such as tribromoboron or trichloroboron. The degree of dealkylation can be controlled by adjusting the equivalent of the dealkylating agent used. For example, 0.5 to 4 equivalents of dealkylating agent can be used to give the compound of formula (I) wherein one, two or all of $R_3$, $R_4$ and $R_5$ are hydrogen.

The dealkylation reaction is preferably carried out at a lower temperature, for example at the temperature between $-100°$ to $0°$ C., preferably from $-81°$ to $-75°$ C., and more preferably $-78°$ C.

If necessary, the compound of the formula (I) can be converted to corresponding pharmaceutically acceptable salts, such as alkali metal salts (e.g. sodium or potassium salts), alkali earth metal salts or ammonium salts.

The compounds of formula (I) can be prepared by utilizing procedures and techniques well known and appreciated by one of ordinary skill in the art. The following examples illustrate one method for preparation of the compounds of formula (I) and are meant by way of illustration and not limitation.

Example 1
3,4,5-trimethoxybenzyl 4-hydroxyphenyl thioether
(1) 3,4,5-trimethoxybenzyl bromide To a 500 ml round-bottom flask under nitrogen were added 15.32 g (0.41 mol) of sodium borohydride and 100 ml of dry tetrahydrofuran. The mixture was stirred for 10 min., then 20 g (0.108 mol) of 3,4,5-trimethoxybenzaldehyde dissolved in 100 ml of tetrahydrofuran was added dropwise to the solution described above. After stirring at room temperature for 16 hr, the solution was cooled to 0° C., 5 ml of distilled water was added dropwise, and the ice-bath was removed. The mixture was stirred overnight. Tetrahydrofuran was concentrated. The mixture was then diluted with 200 ml of water, and extracted twice with 200 ml of diethyl ether. The extract was dried over magnesium sulfate, concentrated after filtration, and dried in vacuum overnight. 3,4,5-Trimethoxybenzyl alcohol (20.2 g, 100% yield) was obtained as a colorless oil, which can be used without further purification.

To a solution of 3,4,5-trimethoxybenzyl alcohol (20.2 g, 0.108 mol) in 300 ml of dry tetrahydrofuran was added 4.12 ml (0.052 mol) of pyridine, and cooled to 0° C. A solution of phosphorous tribromide (4.8 ml, 0.051 mol) in 20 ml of dry tetrahydrofuran was added dropwise to the above solution at 0 ° C. The mixture was stirred for 1 hr. Tetrahydrofuran was concentrated. The residue was then diluted with 200 ml of 10% hydrochloric acid, and then extracted with 200 ml of ethyl acetate. The extract was dried over magnesium sulfate, filtered, concentrated, and dried in vacuum overnight. 3,4,5-Trimethoxybenzyl bromide (27 g, 100% yield) was obtained as a white solid, which can be used without further purification.

(2) 3,4,5-trimethoxybenzyl 4-hydroxyphenyl thioether

4-Hydroxy thiophenol (12 g, 0.095 mol) and potassium carbonate (15.86 g, 0.115 mol) were dissolved in 250 ml of N,N-dimethylformamide, and cooled to 0° C. To the above solution at 0° C. was added dropwise 25 g (0.095 mol) of 3,4,5-trimethoxybenzyl bromide prepared in step (1) dissolved in 50 ml N,N-dimethylformamide. After stirring for 2 hr, the ice-bath was removed, and the solution was stirred overnight. The whole solution was poured into water, and extracted with 300 ml ethyl acetate. The organic layer was washed twice with 300 ml of water. Drying over magnesium sulfate, filtration, concentration, and chromatographic purification on silica gel column (ethyl acetate/n-hexane=2/3) gave 20 g (yield 68%) of 3,4,5-trimethoxybenzyl 4-hydroxyphenyl thioether as a white solid.
M.p.: 139°–140° C.
$^1$H NMR (CDCl$_3$) 3.76 (s, 6H), 3.83 (s, 3H), 3.89 (s, 2H), 5.76 (s, 1H), 6.36 (s, 2H), 6.74 (d, 2H), 7.19 (d, 2H).
MS (EI$^+$) m/e 306.

Elementary analysis ($C_{16}H_{18}O_4S$): calculated: C, 62.70; H, 5.88. Found: C, 62.28; H, 5.93.

Example 2
3,4-dihydroxy-5-methoxybenzyl 4-hydroxyphenyl thioether 3,4,5-Trimethoxybenzyl 4-hydroxyphenyl thioether (3g, 9.8 mmol) prepared as described in Example 1 was dissolved in 60 ml of dry methylene chloride, and cooled to $-78°$ C. Then 2.8 ml (29.5 mmol) of borontribromide in 10 ml of methylene chloride was added dropwise to the above solution. After stirring for 2 hr, the solution was warmed to room temperature, and stirred for another 2 hr (monitored by TLC). Then, the reaction mixture was cooled to 0° C., and added dropwise 50 ml of water. The methylene chloride layer was separated. The crude product, obtained after drying over magnesium sulfate and concentration, was purified on silica gel column chromatography (ethyl acetate/n-hexane=2:1). 3,4-Dihydroxy-5-methoxybenzyl 4-hydroxyphenyl thioether (2.1 g, 77% yield) was obtained as a light yellow solid.
M.P.: 140° C.
$^1$H NMR (DMSO-d$^6$) 3.65 (s, 3H), 3.87 (s, 2H), 6.28 (s, 1H), 6.34 (s, 1H), 6.69 (d, 2H), 7.15 (d, 2H), 8.14 (s, 1H), 8.81 (s, 1H); 9.53 (s, 1H).
MS (EI+) m/e 278.
Elementary analysis ($C_{14}H_{14}O_4S$), calculated: C, 60.43; H, 5.04. Found: C, 60.58; H, 5.17.

Example 3
3,4,5-trimethoxybenzyl 4-hydroxyphenyl sulfoxide 3,4,5-Trimethoxybenzyl 4-hydroxyphenyl thioether (500 mg, 1.63 mmol), prepared as described in Example 1, was dissolved in 10 mlof acetic acid, and heated to 80° C. A solution of chromium trioxide in 30 ml of distilled water was added dropwise to the above solution. The mixture was stirred for 30 min, cooled to room temperature, diluted with 20 ml of water, and then extracted with 30 ml of ethyl acetate. The organic layer was dried over magnesium sulfate, concentrated and purified on silica gel column chromatography (ethyl acetate/n-hexane=¼) to give 348 mg (66% yield) of 3,4,5-trimethoxybenzyl 4-hydroxyphenyl sulfoxide as a white powder.
M.p.: 153° C;
$^1$H NMR( CDCl$_3$) 3.69 (s, 6H), 3.79 (s, 3H), 3.99 (ABq, 2H, J=17 Hz), 6.16 (s, 2H), 6.86 (d, 2H), 7.24 (d, 2H), 8.57 (s, 1H).
MS (EI+) m/e 322.
Elementary analysis ($C_{16}H_{18}O_5S$), calculated: C, 59.62; H, 5.59. Found: C,59.93; H, 5.52.

Example 4
3,4,5-trihydroxybenzyl 4-hydroxyphenyl thioether 3,4,5-Trimethoxybenzyl 4-hydroxyphenyl thioether (12 g, 39.2 mmol), prepared as described in Example 1, was dissolved in 240 ml of dry methylene chloride, and cooled to $-78°$ C. A solution of borontribromide (18.6 ml, 195.6 mmol) in 60 ml of dry methylene chloride was added dropwise to the above solution. The mixture was warmed to room temperature, stirred overnight, cooled to 0° C., and added 300 ml of water. The aqueous layer was then extracted twice with 200 ml of ethyl acetate, dried over magnesium sulfate, concentrated and purified on silica gel column chromatography (ethyl acetate/n-hexane=⅔) to give 8.6 g (77% yield) of 3,4,5-trihydroxybenzyl 4-hydroxyphenyl thioether as a white powder.
M.p.: 158° C.
$^1$H NMR (DMSO-d$^6$) 3.82 (s, 2H), 6.20 (s, 2H), 6.72 (d, 2H), 7.15 (d, 2H), 8.01 (s, 1H), 8.78 (s, 2H), 9.53 (s, 1H).

MS (MI+) m/e 264.
Element analysis ($C_{13}H_{12}O_4S$), calculated: C, 59.09; H, 4.55. Found: C, 58.84; H, 4.71.

Example 5
4-hydroxy-3,5-dimethoxybenzyl 4-hydroxyphenyl thioether 3,4,5-Trimethoxybenzyl 4-hydroxyphenyl thioether (3 g, 9.8 mmol), prepared as described in Example 1, was dissolved in 60 ml of dry methylene chloride, and cooled to −78° C. A solution of borontribromide (2.8 ml, 29.5 mmol) in 10 ml of methylene chloride was added dropwise to the above solution. The mixture was stirred to room temperature, and immediately cooled to 0° C. Water (50 ml) was then added dropwise, and the methylene chloride layer was separated. The crude product, obtained after being dried over magnesium sulfate and concentrated, was purified on silica gel column chromatography (ethyl acetate/n-hexane= ½) to give 1.8 g (63% yield) of 4-hydroxy-3,5-dimethoxybenzyl 4-hydroxyphenyl thioether as a white solid.
M.p.: 128° C;
$^1$H NMR (DMSO-$d^6$)__3.67 (s, 6H), 3.93 (s, 2H), 6.44 (s, 2H), 6.70 (d, 2H), 7.17 (d, 2H), 8.21 (s, 1H), 9.54 (s, 1H).
MS (MI+) m/e 292.
Elementary analysis ($C_{15}H_{16}O_4S$), calculated: C, 61.64; H, 5.48. Found: C, 61.48; H, 5.59.

Example 6
3,4,5-trimethoxybenzyl 3,4-dimethoxyphenyl thioether

Br using a procedure similar to that as described in step (2) of Example 1, the title compound was obtained starting from 3,4-dimethoxy thiophenol (yield 78%).
M.p. : 95° C.
$^1$H NMR (CDCl$_3$)__3.76 (s, 9H), 3.80 (s, 3H), 3.83 (s, 3H), 3.91 (s, 2H), 6.37 (s, 2H), 6.77, 6.94 (dd, 2H), 6.78 (s, 1H).
MS (EI+) m/e 280.
Elementary analysis ($C_{18}H_{22}O_5S$), calculated: C, 61.71; H, 6.29. Found: C, 61.72; H, 6.47.

Example 7
3,4,5-trihydroxybenzyl 3,4-dihydroxyphenyl thioether

By using a procedure similar to that described in Example 2, the title compound was obtained as a white powder starting from the product of Example 6 (yield 48%).
M.p. : 145° C;
$^1$H NMR (DMSO-$d^6$)__3.80 (s, 2H), 6.17 (s, 2H), 6.62 (d, 1H), 6.67 (d, 1H), 6.74 (s, 1H), 7.96 (d, 1H), 8.74 (s, 2H), 8.96 (s, 1H), 8.99 (s, 1H).
MS (EI+) m/e 280.
Elementary analysis ($C_{13}H_{12}O_5S$), calculated: C, 55.71; H, 4.29. Found: C, 55.35; H, 4.37.

The compounds of formula (I) and the pharmaceutically acceptable salts thereof are effective LDL-peroxidation inhibitors, which can lower the LDL and total cholesterol levels and elevate the HDL level in serum.

The pharmacological activities of the compounds of formula (I) may be shown by the following examples.

Example 8
$Cu^{+2}$-induced LDL lipid peroxidation in vitro

50 µl LDL (the cholesterol concentration of which has been adjusted to the plasma range), 5 µM $Cu^{+2}$ and the compounds of formula (I) of various concentrations were added to plastic minivials. The final incubation volume in each assay was adjusted to 100 ul by saline. The mixtures were incubated at 37° C. for 4 hours. The amounts of MDA formed were determined, and $IC_{50}$ were calculated as the amount of compounds needed to inhibit 50% MDS formation. Probucol, a known antioxidant from Sigma Chemicals, was used as control. The results are listed in Table I.

TABLE I

| Compounds | $IC_{50}$ (µM) | Relative Potency (%) |
|---|---|---|
| Probucol | 4.7 | 100 |
| Example 1 | 1.3 | 362 |
| Example 2 | 1.4 | 336 |
| Example 4 | 3.0 | 157 |
| Example 7 | 0.4 | 1146 |

Example 9
Hypocholesterolemic Activity in vivo

Benzafibrate and Gemfibrozil, known hypochloesterolemic agents from Sigma Chemicals, were used as positive controls. A negative control with 1% carboxymethyl cellulose administrated was also used.

Male Balb/c mice, weighted 22 to 24 g, were purchased from Taiwan University Animal Center. During the experiment, the animals were fed with home-made hypercholesterolemic diet (20% casein, 35% butter, 9.1% cellulose, 20.9% dextrose, 4.5% cholesterol, 0.4% cholic acid, 1.8% sodium chloride, 1% vitamins, and 73% water). Then, the positive controls and testing compounds were intraperitoneally given for a consecutive 6 days as a suspension in 1% (w/v) carboxymethyl cellulose at fifth day after mice were given hypercholesterolemic diet. The Bezafibrate, Gemfibrozil and tested compounds were given at a dose of 100 mg/kg/day and 20 ml/kg in mice. The body weight of mice was recorded at the beginning of experiment and before fasting the animal. The food consumption were also recorded daily during hypercholesterolemic diet treatment period.

After four hours from the last dose administration, the animals were fasted for 16 hours, sacrificed, and, then, blood samples were collected from the animals. The blood samples were allowed to stand for 30 min, and, then, centrifuged at 3000 rpm for 10 min to obtain serum. The serum was stored at 4° C. before use. The total cholesterol and triglyceride levels were enzymatically measured using Boehringer Mannhein kits No. 816302 and 816370. The HDL-cholesterol level was also enzymatically determined with Boehringer Mannhein kit No. 543004. The LDL cholesterol was calculated in accordance with the equation below:

Total cholesterol−Triglyceride/5−HDL cholesterol=LDL cholesterol

The significance of differences among the total cholesterol, triglyceride, HDL-cholesterol and LDL-cholesterol of the control and that of treated groups were determined using t-test were shown in Table II.

TABLE II

| Drug | Total chol. (mg/dl) | Triglyceride. (mg/dl) | HDL/chol. (mg/dl) | LDL/chol. (mg/dl) |
|---|---|---|---|---|
| Control | $^a$75.56 ± 3.56 $^b$(100%) | 59.53 ± 3.83 (100%) | 53.80 ± 2.1 (100%) | 31.50 ± 2.3 (100%) |
| Bezafibrate | **64.06 ± 5.87 $^c$(−15%) | **49.78 ± 3.22 (−16%) | *62.60 ± 7.70 (+16%) | *26.70 ± 2.70 (−16%) |
| Gemfibrozil | *69.77 ± 2.88 | *52.14 ± 3.34 | *58.70 ± 2.90 | *27.00 ± 3.4 |

TABLE II-continued

| Drug | Total chol. (mg/dl) | Tri-glyceride. (mg/dl) | HDL/chol. (mg/dl) | LDL/chol. (mg/dl) |
|---|---|---|---|---|
| ZYF9053 | (−8%) *64.75 ± 7.70 | (−12%) *51.53 ± 2.71 | (+9%) *57.10 ± 1.60 | (−15%) *27.60 ± 1.70 |
| ZYF9067 | (−14%) 79.83 ± 7.57 (+6%) | (−13%) 53.58 ± 4.54 (−10%) | (+6%) *59.50 ± 3.50 (+11%) | (−12%) *26.70 ± 4.30 (−15%) |

[a]: Data are expressed as mean ± SD. Each treatment has 6 mice. *P ≤ 0.05; **P ≤ 0.01
[b]: The total cholesterol (total chol.), triglyceride, HDL-cholesterol (HDL-chol.) and LDL-cholesterol (LDL-chol.) are expressed as 100% compared to that of treated group.
[c]: The inhibition or activating percentage is expressed as [1-(treated group/control group)] × 100%.

As shown in the above results, the compounds of formula (I) and the pharmaceutically acceptable salts thereof are effective antiatherosclerosis agents. They are not only potent LDL-peroxidation inhibitors, but also lower the total cholesterol, LDL-cholesterol and triglyceride levels, and elevate the HDL-cholesterol level in serum. Therefore, they are useful for the prevention, treatment, or inhibition of hypercholesterolemia, hyperlipidemia and atherosclerosis.

When compounds of the formula (I) and the pharmaceutically acceptable salts thereof are used in treating or inhibiting the diseases described above, they can be administrated directly or in the form of pharmaceutical compositions containing an effective amount of the compounds of the formula (I) as the active ingredient.

As used herein, the term "effective amount" refers to an amount that is effective in inhibiting LDL-peroxidation and/or lowering serum total cholesterol and/or serum LDL levels and/or elevating serum HDL level and/or treating or inhibiting hypercholesterolemia and/or hyperlipidemia and/or atherosclerosis. It should be understood that the treatments for atherosclerosis can include effectively preventing, slowing, interrupting, arresting or stopping atherosclerotic lesion or plaque development or growth and does not necessarily require a total elimination of atherosclerosis.

It is appreciated by those skilled in the art that the effective amount described above varies along with many factors, such as the species, age, body weight and general health of patients; the diseases to be treated or the degree or the severity thereof; the specific diseases involved; the particular compound administered; the mode and the frequency of administration; and the desired efficiency.

In general, the daily dosage of the compounds of formula (I) and the pharmaceutically acceptable salts thereof is about 20 to 40 mg/kg of body weight.

Depending on the routes of administration, the compounds of formula (I) may be used in combination with various pharmaceutically acceptable carries, adjuvants and diluents and other active ingredients, to produce various preparations, including oral or parenteral dosage forms.

The dosage forms suitable for oral administration include tablets, capsules, powders, pills, solutions, buccal tablets, chewable tablets, syrups, suspensions and emulsions.

The solid dosage forms for oral administration may contain one or more of the following adjuvants: binders, such as micro crystalline cellulose, tragacanth gum or gelatin; excipients, such as starch or lactose; disintegrating agents, such as alginic acids, corn starch etc.; lubricants, such as magnesium stearate; sweetening agents, such as sucrose or saccharin; and flavoring agents, such as peppermint or orange flavoring.

In addition to the adjuvants described above, the pharmaceutical composition in a tablet form may also contain a liquid carrier, such as polyethylene glycol or fatty oil.

A solid oral dosage form may also contain materials which modify the physical form of the unit dosage form. For example, the dosage form may contain a coating, e.g. a sugar coating, shellac gum coating or enteric coating.

In addition to the compounds of formula (I) and the pharmaceutically acceptable salts thereof, the liquid dosage form for oral administration may also contain colorings, flavors, sweetening agents and preservatives.

Dosage forms suitable for parenteral administration include solutions or suspensions, which may contain one or more of the following adjuvants: sterile diluents, such as water for injection, oils, dextrose, saline solution, polyethylene glycol or other synthetic solvents; antibacterial agents, such as benzyl alcohol, or methyl- or propyl- paraben and chlorobutanol; antioxidants, such as ascorbic acid or sodium hypobismuthite; chelating agents, such as EDTA; buffers, such as acetates, citrates or phosphates, etc.

The formulations for parenteral administration can be contained in glass or plastic ampules, disposable syringes or multiple-dose vials.

In general, pharmaceutical compositions of the invention comprise an effective amount of the compounds of formula (I) or the pharmaceutically acceptable salts thereof, and at least one of the above pharmaceutically acceptable carriers or adjuvants.

The characteristics of the invention have been illustrated herein above. It is recognized that one of ordinary skill may perform various modifications without departing from the spirit and scope of the invention.

What is claimed is:

1. A compound having the general formula:

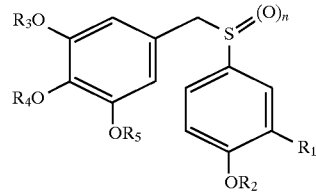

wherein
$R_1$ represents hydrogen, hydroxy or alkoxy;
$R_2$, $R_3$, $R_4$ and $R_5$ may be hydrogen or alkyl; and n is 0,1 or 2;
and the pharmaceutically acceptable salts thereof, wherein when n is 0 or 2 and $R_3$, $R_4$, and $R_5$ are alkyl, one of $R_1$ or $R_2$ is not hydrogen.

2. A compound according to claim 1, selected from the group consisting of 3, 4, 5-trimethoxybenzyl 4-hydroxyphenyl thioether;

3, 4-dihydroxy-5-methoxybenzyl 4-hydroxyphenyl thioether;

3, 4, 5-trimethoxybenzyl 4-hydroxyphenyl sulfoxide;

3, 4, 5-trihydroxybenzyl 4-hydroxyphenyl thioether;

4-hydroxy-3, 5-dimethoxybenzyl 4-hydroxyphenyl thioether;

3, 4, 5-trimethoxybenzyl 3, 4-dimethoxyphenyl thioether; and 3, 4, 5-trihydroxybenzyl 3, 4-dihydroxyphenyl thioether.

3. A pharmaceutical comprising at least one compound having the general formula:

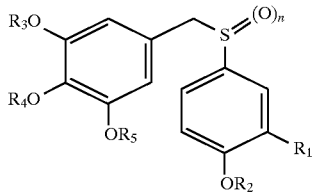

wherein $R_1$ represents hydrogen, hydroxy or alkoxy;

$R_2$, $R_3$, $R_4$ and $R_5$ may be hydrogen or alkyl; and n is 0, 1 or 2;

and a pharmaceutically acceptable carrier, adjuvant or diluent thereof.

4. A pharmaceutical comprising at least one compound of claim 2, and a pharmaceutically acceptable carrier, adjuvant or diluent thereof.

5. A method for inhibiting LDL-peroxidation comprising contacting LDL with at least one compound according to claim 1.

6. A method for inhibiting LDL-peroxidation comprising contacting LDL with at least one compound according to claim 2.

7. A method for inhibiting atherosclerosis, hyperholesterolemia or hyperlipidemia comprising contacting LDL with at least one compound according to claim 1.

8. A method for inhibiting atherosclerosis, hyperholesterolemia or hyperlipidemia comprising contacting LDL with at least one compound according to claim 2.

9. A method for treating atherosclerosis, hypercholesterolemia or hyper-lipidemia comprising administering an effective atherosclerosis, hypercholesterolemia or hyperipidemia inhibiting amount of at least one compound of claim 1.

10. A method for treating atherosclerosis, hypercholesterolemia or hyper-lipidemia comprising administering an effective atherosclerosis, hypercholesterolemia or hyperipidemia inhibiting amount of at least one compound of claim 2.

11. A method for inhibiting LDL-peroxidation comprising contacting LDL with a pharmaceutical according to claim 3.

12. A method for inhibiting atherosclerosis, hyperholesterolemia or hyperlipidemia comprising contacting LDL with a pharmaceutical according to claim 3.

13. A method for treating atherosclerosis, hypercholesterolemia or hyper-lipidemia comprising administering an effective atherosclerosis, hypercholesterolemia or hyperipidemia inhibiting amount of a pharmaceutical of claim 3.

* * * * *